United States Patent [19]

Genco et al.

[11] 4,397,554
[45] Aug. 9, 1983

[54] TRANSPARENCY HALATION MEASUREMENT METHOD AND APPARATUS

[75] Inventors: Louis V. Genco, Enon; Robert G. Eggleston, Oxford, both of Ohio

[73] Assignee: The United States of America as represented by the Secretary of the Air Force, Washington, D.C.

[21] Appl. No.: 251,823

[22] Filed: Apr. 7, 1981

[51] Int. Cl.³ ............................................. G01N 23/04
[52] U.S. Cl. .................................... 356/239; 250/572
[58] Field of Search ............... 356/337, 340, 129, 362, 356/239, 430, 240; 250/572, 571; 350/162.11, 276 R

[56] References Cited

U.S. PATENT DOCUMENTS

| | | | |
|---|---|---|---|
| 3,025,749 | 3/1962 | Rodman et al. | 356/239 |
| 3,614,232 | 10/1971 | Mathisen | 356/239 |
| 4,310,242 | 1/1982 | Genco et al. | 356/239 |

Primary Examiner—Bruce Y. Arnold
Attorney, Agent, or Firm—Donald J. Singer; John R. Flanagan

[57] ABSTRACT

For determining the extent of surface deterioration of a transparency, a method and apparatus is provided for measuring light scatter or halation produced by the deterioration. An intense light source is placed on one side of the transparency to be tested, and a camera and annular neutral density filter are positioned on the opposite side. The filter is aligned between the light source and camera lens so as to occlude or shade the lens from the direct light rays, whereby light scattered by portions of the transparency outside the periphery of the filter may be recorded on photographic film in the camera. The annular filter contains contrasting rings of varying shades of grey which facilitate standardization of halation measurements made on different transparencies or on the same transparency at different periods in its life cycle.

8 Claims, 6 Drawing Figures

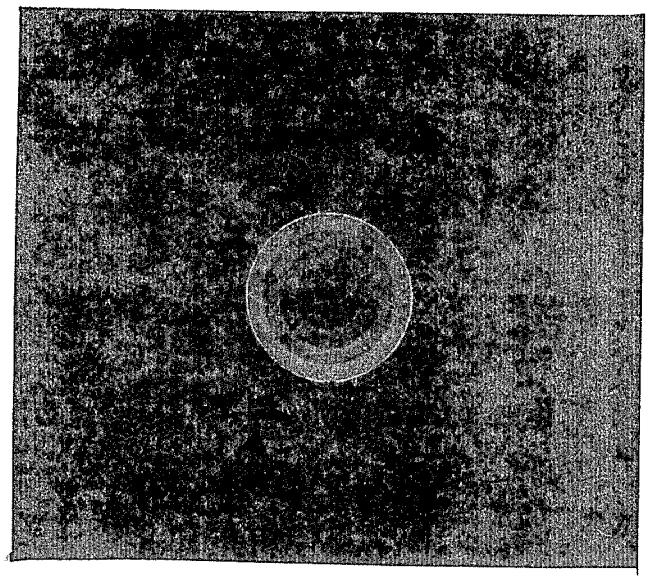
Fig. 3
Fig. 4
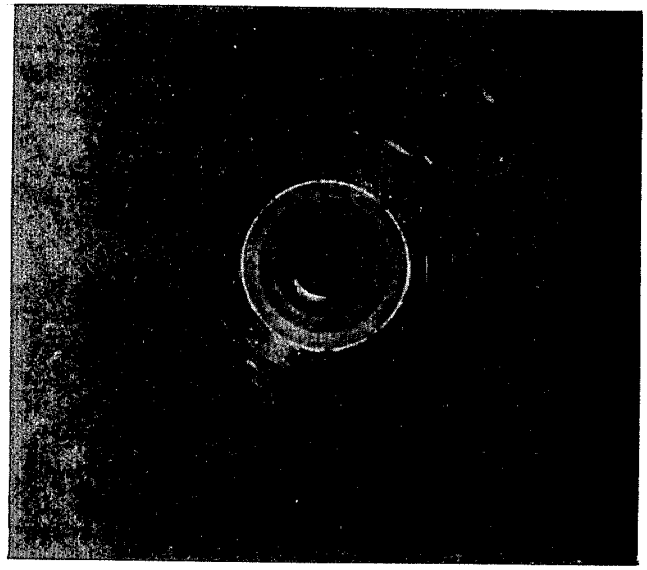
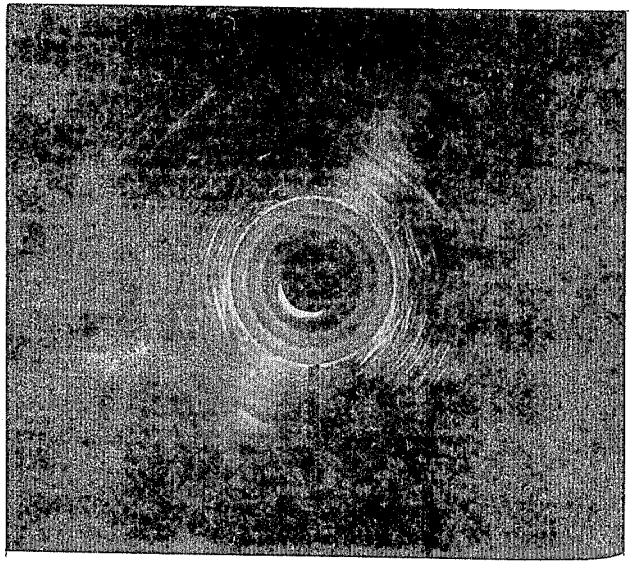
Fig. 5

TRANSPARENCY HALATION MEASUREMENT METHOD AND APPARATUS

RIGHTS OF THE GOVERNMENT

The invention described herein may be manufactured and used by or for the Government of the United States for all governmental purposes without the payment of any royalty.

BACKGROUND OF THE INVENTION

1. Field of the Invention

The present invention broadly relates to measuring the amount of extent of halation due to surface deterioration in transparencies, such as aircraft windscreens made of plastic or the like, and, more particularly, is concerned with a method and apparatus for providing a record of the halation measurement in terms of human visual perception, i.e., as a person would see the tested region of the transparency were he to visually inspect the transparency.

2. Description of the Prior art.

The requirement for effective birdstrike protection in todays's high-performance aircraft has caused a transition from glass canopies and windscreens to laminated or monolithic plastic transparencies. Plastic aircraft transparencies have a life cycle which appears to be limitedby the surface qualities of the transparency. Since the hardness of the plastic surface is less than that of glass, the plastic transparencies are much more susceptible to environmental surface damage than the glass transparencies which they replace.

One of the most significant optical changes that occurs during the life cycle of the plastic transparency is an increase in haze or halation due to the surface deterioration of the transparency. As halation increases, light appears to "spread" from its source, causing a disabling glare or significant reduction in contrast of objects seen through the transparency. This disabling glare can lead to flight safety problems as the pilot's view of the external world is restricted.

Halation, the spreading of light beyond its proper boundaries due to internal reflections from scratches, is evident whenever a bright light source appears in the field of view of the pilot. Some of the light scatter occurs in the pilot's eye, and is often perceived as a dim halo or ring of light encircling the light source as it is viewed at night. Another source of halation is the "volume haze" inherent in most aircraft transparencies. A third, and probably most significant source of halation is the accumulation of scratches on the surface of the transparencies. The effect of aging on a transparency is due to this source of halation. These scratches tend to cause light to be more evenly distributed over the surface of the transparency, resulting in disabling glare or reduction of contrast between a target and its background. SInce the human eye is a contrast detector, and since target acquisition and tracking are based on maintaining sufficient contrast for the visual system to be operative, reduction in contrast will reduce the ability of the pilot to see objects through the transparency. If the disabling glare is sufficiently widespread, portions of the transparency may become unusable which results in effectively reducing the visual field of the pilot. The loss of visual field can lead to flight safety problems and loss of combat effectiveness.

Current methods of measuring haze are limited to measuring volume haze only. Even then, the measurement methods can only be performed on small, flat transparency samples held in a specific relationship to the measuring device. The methods are neither suitable for the measurement of surface scratch induced haze, nor do they depict the appearance or the effect of halation on the pilot's visual abilities.

These methods of measuring haze commonly use an integrating sphere type hazemeter instrument. (One such instrument is called the Gardner Hazemeter.) After calibration of the instrument, a small sample of the transparent material is placed in front of the sphere aperture, and a reading is taken of all of the light impingent on the inner surface of the sphere. A second reading is taken while the non-diffused light is allowed to exit the sphere or fall into a light trap. The haze measurement, in percent, is then calculated from a ratio of the two readings. Although this is an effective method of comparing the "haze" of various transparent materials, it can not and does not accurately predict the visual effect upon the observer.

The above-described measurement method has significant disadvantages for field use. First, the sample to be tested must be held perpendicular to the aperture, so that all readings are taken along an axis which is normal to the surface of the transparency. Next, the sample must contain no surface scratches. If the sample does contain scratches, they should be removed by immersing the sample in a liquid of equal index of refraction. Finally, the surface of the sample must be flat and in contact with the aperture of the test instrument.

Some of these disadvantages have been overcome by several transparency manufacturers and the Air Force Aerospace Medical Research Lab through modification of their Gardner Hazemeters to accept large transparencies. These modifications have allowed haze readings to be taken over virtually the entire surface of a slightly curved transparency, and over a lesser area of a significantly curved transparency. However, measurement errors may be exacerbated by the remaining disadvantages mentioned above. In any case, modification of hazemeters has not allowed halation measurements to be taken under field conditions, while the transparency remained on the aircraft. Furthermore, no real relationship had been shown between haze as measured by the ASTM or FTM methods and visual performance. Finally, the instrumentation is bulky and for that reason too is not suited for use under field conditions.

In summary, at the present time there is no apparatus available to objectively measure the effect of halation upon vision, nor reliably measure the extent of halation in aircraft windscreens, canopies or any large or curved transparencies. Thus, there is no objective metric to indicate the extent of visual hazards due to halation, nor to indicate a proper time for removal and replacement of the transparency.

SUMMARY OF THE INVENTION

The present invention substantially overcomes the above-mentioned disadvantages of current methods by providing a method and apparatus for measuring the halation present in any transparency mounted in any position, independent of curvature, shape, thickness or any other of its physical parameters, but related to the visual percept of disabling glare associated with the haze. Thus, the present invention will provide a record which will portray the optical degradation resulting from surface deterioration in the transparency in terms which are predictive of the effect of halation or haze on the visual processes of individuals looking through the transparency. Also, the apparatus may be made portable, performs tests which are reliable, accurate and repeatable, and may be used under most field and laboratory conditions by non-scientific or technical personnel. The record produced by the present invention can be used to provide evidence of halation caused by surface deterioration, track the changes in halation with time, and provide an indicator for repair or replacement of the transparency.

Accordingly, the present invention broadly provides a method and apparatus for measuring the extent of halation present in a transparency which involves: (a) projecting light through a given test region of a transparency from a light source positioned on one side of the transparency; (b) disposing a camera on an opposite side of the transparency with its lens aligned with the light source for receiving light which passes through the transparency test region on a photographic film within the camera; and (c) interposing a filter in the light path between the light source and the lens of the camera, the filter having an opaque central portion serving to occlude from the camera lens the direct light rays from the light source. In such manner, a record of the halation present in the test region of the transparency outside the periphery of the filter is provided on the photographic film which when processed will be very similar to that which would be seen by an observed looking through the test region on the transparency at the light source.

More particularly, the filter has a plurality of annular concentric rings of varying shades of grey about the opaque central portion which act as a calibration standard for the photographic print developer. Furthermore, the filter is positioned as close to the transparency as possible in order to occlude the direct light rays of the light source from the camera lens and thereby reduce the possibility of causing halation in the camera lens which would interfere with the measurement of halation in the transparency.

BRIEF DESCRIPTION OF THE DRAWING

FIG. 3 is a view of the apparatus similar to FIG. 1, but with a transparency positioned in front of the filter.

FIG. 4 is a photograph similar to the one of FIG. 2, but taken with the transparency present as shown in FIG. 3 and depicting relatively slight halation in the transparency.

FIG. 5 is another photograph similar to the one of FIG. 4, but of a different transparency having a relatively greater extent of halation than the transparency of FIG. 4 at their respective regions that were tested.

DETAILED DESCRIPTION OF THE INVENTION

Figure 1:
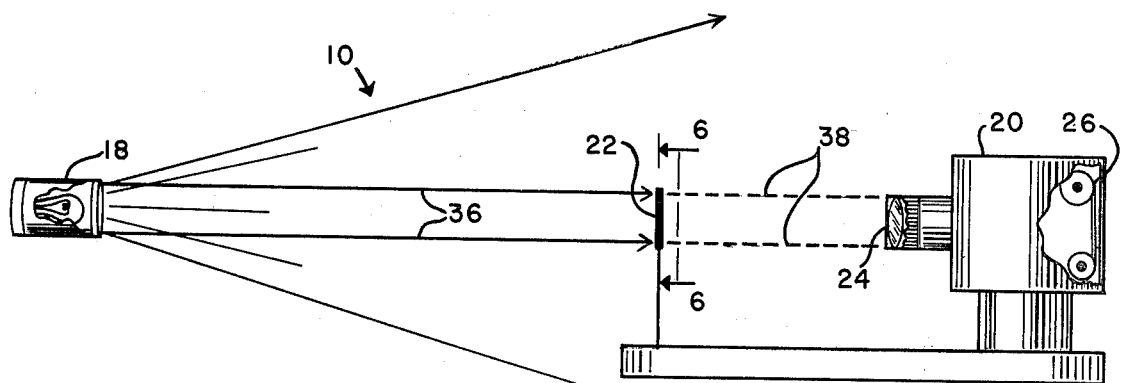
FIG. 1 is a side elevational view in schematical form of the transparency halation measurement apparatus of the present invention without the transparency being present.
Figure 2:
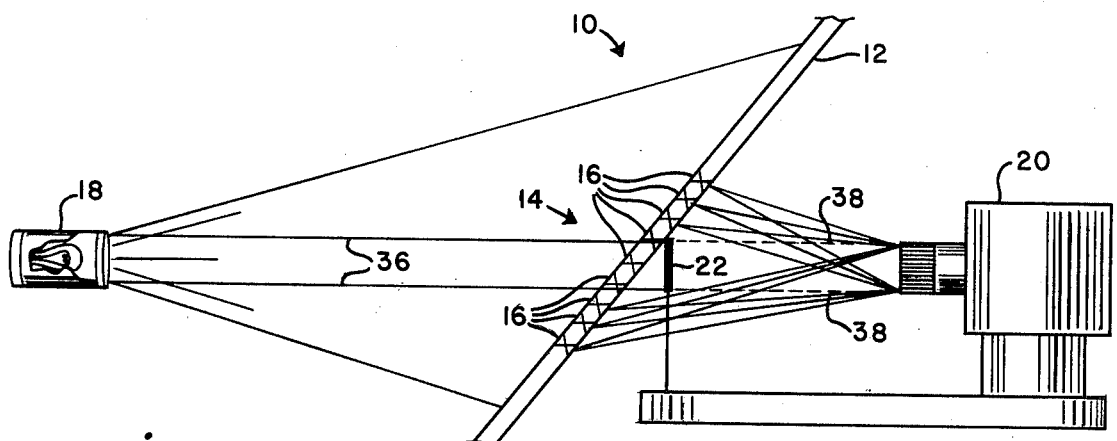
FIG. 2 is a calibration photograph of the annular filter positioned between the light source and camera of the apparatus, without the transparency being present, as seen in FIG. 1.

Referring now to the drawings, and particularly to FIGS. 1 and 3, there is shown the preferred embodiment of the halation measurement apparatus of the present invention, being generally designated 10. In FIG. 1, the apparatus 10, is set up for taking a picture from which the calibration photograph seen in FIG. 2 may be developed. In FIG. 3, the apparatus 10 is set up proximate a transparency 12, such as an aircraft windscreen, for testing a region, generally designated 14, thereof which contains scratches 16 or other elements which cause scattering or spreading of light incident thereon.

Basically, the halation measurement apparatus 10 includes a light source 18, a camera 20, and an annular filter 22 positioned between the light source and camera. When testing the transparency 12, camera 20 is placed at the design eye position of the transparency and the annular filter 22 is disposed behind, but as close as possible to, the transparency as seen in FIG. 3. The light source 18, which preferably takes the form of a high intensity photograhic stroboscope, is placed a sufficient distance from the transparency 12, such as within 20 to 30 feet, so as to insure that nearly collimated light rays strike the front surface of the transparency. The annular filter 22 is aligned with the light source 18 and a lens 24 of the camera 20 so as to block the lighpath therebetween. Therefore, when testing a region 14 of the transparency 12 which contains surface scratches 16, only light spreading from scratches located outside the periphery of the filter 22 may reach the camera 20, pass through its lens 24 and strike the surface of photographic film 26 contained in the camera. The direct portion of the light from the light source 18 strikes the annular filter 22 and is blocked from reaching the camera lens 24.

Figure 6:
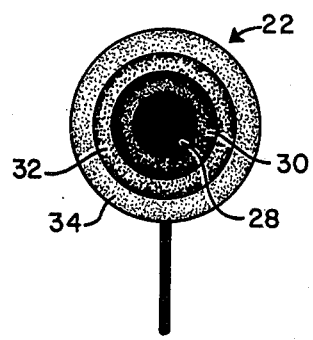
FIG. 6 is an enlarged rear elevation view of the filter as seen along 6—6 of FIG. 1.

More particularly, as depicted in FIG. 6, the filter 22 is a neutral density filter disc having a central opaque portion 28 with three rings 30, 32 and 34 concentrically encircling the central portion. Each ring decreases in opacity relative to the central portion 26 the greater its distance from the central portion. The central opaque portion 28 serves to occlude the intense direct light rays emitted from the light source 18 from striking the lens 24 of the camera 20. Overall, the filter 22 substantially blocks the bundle of direct light rays bounded by rays 36 and thereby casts a shadow falling between dashed lines 38 in FIGS. 1 and 3. This reduces the possibility of causing halation in the camers lens 24, which would interfere with the measurement of halation in the transparency.

The densities of the inner, middle and outer ring 30, 32 and 34 of the annular filter 22 are 1.13, 1.70, and 2.36, respectively. The densities of the rings were chosen empirically to provide a readily visible contrast between them so that, in addition to acting as a lens shield, the neutral density filter 22 acts as a calibration standard for the photograph developer. All photographic prints containing a picture of the filter may then be developed so as to maintain perceptual equality from print to print of the contrasting grey shades comprising the filter rings. This was substantially achieved in development of the photographs in FIGS. 2, 4 and 5. The filter provides a convenient visible reference to use during the development and inspection process. Additionally, experimentation has shown that accurate visual inspection is sufficient to insure equality between prints, and that equality can be accomplished without great difficulty. Maintenance of the grey shade equality is extremely important in the test method and apparatus of the present invention since it is the only way in which to insure standardization of the photographs.

The amount of light reaching the film 26 during testing is influenced by several variables, among which are light source output, transparency haze, transparency light attenuation (absorption), camera f-stop, and exposure duration for print development. The calibrated neutral density filter 22 allows the photographic film procesor to compensate for all of the non-haze or -halation related variables, and insure an accurate, repeatable relative measure of the effects of halation on the camera image. If the filter's rings appear equal in contrast and greyness from print to print, an equal amount of light must have exposed the film in the region of the filter for all prints. If this exposure is kept constant, any change in the halation pattern (rings of light) outside of the area of the filter disc must be due solely to light scattering or spread in the transparency. One can now correctly assume that it is the filter which is the critical element in the measurement apparatus and method, and that non-standardized light sources and camera may well be used, while still achieving equivalent results. In fact, equivalent results may be obtained through transparencies of different transmission values, thus making it possible to compare relatively high absorptive transparencies with those whose absorption characteristics are relatively low. Also, slight errors in photographic exposure can be corrected in the final print, thereby allowing the field technician some margin or tolerance in exposure.

As mentioned above, the preferred embodiment of the apparatus uses a conventional photographic stroboscope as the light source 18. The high intensity output of this light source allows small camera apertures to be used (large f-stops), thus reducing the effect of stray ambient light. With this light source, tests need not be conducted in absolute darkness since the shutter and light are synchronized. Also, since the camera, filter and light source must be accurately aligned, the stroboscope is preferably modified to include a small incandescent lamp (not shown) which acts as a visible target. With the camera 20 at design eye position and using the target light of the stroboscope, the position of the strobe light source and annular filter can be readily adjusted so that they share a common optical axis with the camera lens.

In a practical embodiment of the apparatus of the present invention, the camera chosen for use was an Olympus OM-1 single-lens reflex equipped with a 50 mm lens. The choice of this camera allows the photographer to accurately align the camera with the center of the filter and light source. Also, the choice of photographic film type is of some importance. If films of different gammas or contrast ranges are selected, their results may not be compatible. For purposes of standardization, in a practical embodiment of the apparatus Kodak Plus-X film was used and developed in a Kodak D-76 developer. Furthermore, contrast ranges among photographic papers can differ significantly. If photographs of the same subject are printed on papers of different contrasts, the appearance of the final prints may differ enough to cause a matching or calibration error. One type of paper which may be used is Kodak Rapid 2 Polycontrast (Type F) paper, exposed without a contrast filter, and developed in a Kodak Dektol developer.

It is thought that the present invention and many of its attendant advantages will be understood from the foregoing description and it will be apparent that various changes may be made in the steps of the method, and form, construction and arangement of the parts of the apparatus, described without departing from the spirit and scope of the invention or sacrificing all of its material advantages, the form hereinbefore described being merely a preferred exemplary embodiment thereof.

Having thus described the invention what is claimed is:

1. A method of measuring halation in a transparency, comprising the steps of:
    (a) projecting light through a given test region of a transparency from a light source positioned on one side of said transparency;
    (b) disposing a camera on an opposite side of said transparency with its lens aligned with said light source for receiving light which passes through said transparency test region to produce an image on a photographic film within said camera; and
    (c) interposing a filter in the light path between said light source and said lens of said camera, said filter serving to occlude from said camera lens the direct light from said light source such that an image of halation present in said test region of said transparency outside the periphery of said filter may be recorded on said photographic film of said camera.

2. The halation measuring method as recited in claim 1, further comprising the step of:
    (d) photographing said image of halation present in said transparency test region of said photographic film in said camera; and
    (e) developing said film to produce a visible photographic record of halation in said transparency test region.

3. The halation measuring method as recited in claim 2, wherein said photographing of said image of halation also serves to record an image of said filter on said film which, when developed into a visible photograhic record along with said halation image may be compared to a calibration photograph of said filter for facilitating standardization of halation measurements.

4. A method of recording a calibration standard for measuring halation in a transparency, comprising the steps of:
    (a) projecting light from a light source toward a lens of a camera;
    (b) interposing a filter in the light path between the source of said light and said lens of said camera such that direct light from said light source is occluded from said camera lens, said filter having a central opaque portion with a plurality of rings concentrically encircling said central portion and diminishing in opacity the greater distance each ring is from said central portion;
    (c) photographing an image of said filter on film in said camera; and
    (d) producing a photographic print of said filter image for use as a calibration standard in which the contrast between various rings of said plurality of rings of said filter is readily visible on said print.

5. Apparatus for measuring halation in a transparency comprising:
    (a) a light source positioned on one side of a transparency for projecting light through a given test region of said transparency;
    (b) a camera disposed on the opposite side of said transparency, said camera containing photograhic film and having a lens aligned with said light source for receiving light which passes through said transparency test region to produce an image on said film within said camera; and (c) a filter interposed in the light path between said light source and said camera lens, said filter serving to occlude from said camera lens the direct light from said light source such that an image of halation present in said test region of said transparency outside the periphery of said filter may be recorded on said photographic film of said camera.

6. The apparatus of claim 5, wherein said filter has a central opaque portion with a plurality of rings concentrically encircling said central portion and diminishing in opacity the greater distance each ring is from said central portion, whereby an image of said filter is recorded on said film with said image of halation surrounding said filter image.

7. The apparatus of claim 5, wherein said filter has a central portion and at least one ring surrounding said central portion, said ring having a degree of opacity sufficiently different from said central portion so that the contrast between the two is readily visible to the human eye.

8. The apparatus of claim 7, wherein an image of said filter is recorded on said film along with said image of said halation in said transparency, said filter image facilitating standardization of halation measurements.

* * * * *

UNITED STATES PATENT AND TRADEMARK OFFICE
CERTIFICATE OF CORRECTION

PATENT NO. : 4,397,554

DATED : August 9, 1983

INVENTOR(S) : Louis V. Genco and Robert G. Eggleston

It is certified that error appears in the above—identified patent and that said Letters Patent is hereby corrected as shown below:

Col. 1, line 14, delete "of" and insert -- or --; line 28, delete "limitedby" and insert -- limited by --; and line 57, delete "SInce" and insert -- since --. Col. 5, line 7, delete "procesor" and insert -- processor --. Col. 6, line 29 (claim 2, line 4), delete "of" and insert -- on --.

Signed and Sealed this

Sixth Day of December 1983

[SEAL]

Attest:

GERALD J. MOSSINGHOFF

Attesting Officer

Commissioner of Patents and Trademarks